United States Patent
Jang et al.

(10) Patent No.: US 10,842,992 B2
(45) Date of Patent: Nov. 24, 2020

(54) ACTIVE CARDIAC ELECTRICAL LEAD

(71) Applicant: MICROPORT SOARING CRM (SHANGHAI) CO., LTD., Shanghai (CN)

(72) Inventors: Grace Jang, Shanghai (CN); Zhijun Cheng, Shanghai (CN); Jiangkai Sun, Shanghai (CN)

(73) Assignee: MICROPORT SOARING CRM (SHANGHAI) CO., LTD., Shanghai (CN)

( * ) Notice: Subject to any disclaimer, the term of this patent is extended or adjusted under 35 U.S.C. 154(b) by 124 days.

(21) Appl. No.: 15/771,817

(22) PCT Filed: Oct. 27, 2016

(86) PCT No.: PCT/CN2016/103628
§ 371 (c)(1),
(2) Date: Apr. 27, 2018

(87) PCT Pub. No.: WO2017/071621
PCT Pub. Date: May 4, 2017

(65) Prior Publication Data
US 2018/0311495 A1    Nov. 1, 2018

(30) Foreign Application Priority Data
Oct. 29, 2015    (CN) .......................... 2015 1 0719424

(51) Int. Cl.
*A61N 1/05*    (2006.01)
*A61N 1/00*    (2006.01)
*A61N 1/362*    (2006.01)

(52) U.S. Cl.
CPC ................ *A61N 1/056* (2013.01); *A61N 1/00* (2013.01); *A61N 1/059* (2013.01); *A61N 1/0573* (2013.01); *A61N 1/3629* (2017.08)

(58) Field of Classification Search
CPC ....... A61N 1/0573; A61N 1/059; A61N 1/362
See application file for complete search history.

(56) References Cited

U.S. PATENT DOCUMENTS

| 7,383,091 | B1 | 6/2008 | Chitre et al. | |
| 2012/0130220 | A1* | 5/2012 | Maskara | A61N 1/056 600/374 |
| 2014/0296955 | A1* | 10/2014 | Jang | A61N 1/0573 607/127 |

FOREIGN PATENT DOCUMENTS

| CN | 201329130 Y | 10/2009 |
| CN | 202289222 U | 7/2012 |
| CN | 103635227 A | 3/2014 |
| CN | 103635227 A | 3/2014 |
| WO | WO2008074026 A2 | 6/2008 |

\* cited by examiner

*Primary Examiner* — Catherine M Voorhees
*Assistant Examiner* — Roland Dinga
(74) *Attorney, Agent, or Firm* — Muncy, Geissler, Olds & Lowe, PC

(57) ABSTRACT

An active cardiac electrical lead is disclosed, including a tip housing having a lumen, a soft tip plug and a marker band. The tip housing includes a body and an extension extending from a distal end of the body, and the body is of greater outer diameter than the extension. The soft tip plug fits over the extension and engaging the extension. The marker band is attached to an outer surface of the body or to an inner surface of the lumen.

15 Claims, 8 Drawing Sheets

ACTIVE CARDIAC ELECTRICAL LEAD

TECHNICAL FIELD

This application relates to the field of medical devices and, in particular, to an active cardiac electrical lead.

BACKGROUND

Leads are often used to stimulate the heart to contract. For example, when a patient's heart is functioning with an abnormal rhythm, electrical energy may be applied to the heart via the leads to restore the heart to a normal rhythm. In some cases, this procedure may be an isolated event, while in other cases, a more frequent, regular, or even continuous process may occur. In these cases, leads may be incorporated with a pacemaker, defibrillator, or other electrical stimulation device to transmit the pacing pulses to atrium or ventricle of a heart. The system including the electrical stimulation device and the lead is implantable and used for a long time.

In general, a lead includes a pair of electrodes disposed at a distal end of the lead which may be positioned in the right ventricle or the right atrium of the heart. The proximal end of the lead may be coupled to a defibrillator or a pacemaker and conductors can deliver electrical impulses along the length of the lead to the electrode, thereby delivering pacing pulses to the heart.

There are two conventional types of leads. The first type of leads is referred to as an active electrical lead with an active mechanism at the distal end. The second type of leads is referred to as a passive electrical lead with a passive mechanism at the distal end.

The distal end of a typical active electrical lead may include a helical anchor electrode designed to be actuated and axially extend and/or rotate out of a tip portion of the lead to engage or embed into the endocardium. The distal end of a typical passive electrical lead may include an anchor type fixation mechanism designed to anchor the distal end in the heart. The fixation mechanism for a passive lead, for example, may include one or more radially spaced tines that secure the distal end in the heart.

The proximal end of pacemaker and defibrillator leads are commonly designed and manufactured according to the standards such as YY/T 0491-2004 and ISO 5841-3, 2000. The standard is applicable to both active and passive pacemaker or defibrillator leads. Within that standard, medical device companies commonly have their own unique designs. Among the technologies used to meet the standards, laser welding and metal crimping are used to get a highly reliable joint connections for pacemaker and defibrillator leads.

The design of defibrillator and pacemaker leads has evolved over time. At present, the proximal end of an active electrical lead and the proximal end of a passive electrical lead are generally designed differently due to their functional differences. That is, the proximal end of an active lead may be designed to actuate and/or control distal active mechanism, while the proximal end of a passive lead may not include such actuation and/or control features. System designs and assembly processes of the passive and active electrical leads are, thus, different. As a result, the overall cost for which having significant different system designs and assembly processes is relatively high.

With Patent Application No. PCT/CN2012/077783 as an example, specifically with reference to FIGS. 1 and 2 thereof, an active cardiac electrical lead is disclosed, which has a tip housing 100' inlaid with a marker band 120' to determine the distance that a helical anchor electrode 140' extends out of or retract into the tip housing 100'. In fact, the marker band 120' is injection-molded into the tip housing 100'. Since this part is small in size and has a relatively sophisticated structure necessary to realize the desired functions, and the implantable-grade PU material has poor performance for injection molding, it's very difficult to manufacture the tip housing with the required dimensional accuracy. This may lead to a low yield and a high cost. In addition, in order to minimize trauma to vasculature and tissue caused by the implantation of the electrical lead, a soft tip plug 110' connects to a distal end of the tip housing. In order to satisfy the bonding requirement for the soft tip plug 110' and the tip housing 100' and the marker band 120', four tip bores (not labeled in the figures) are arranged in the tip housing 100'. Specifically, the soft tip plug 110' includes a plurality of radially-extending plugs configured to insert into and retention within the tip bore in the tip housing 100'. The marker band 120' is insert-molded into the tip housing 100' and a plurality of retention posts are molded to extend from an inner wall of the tip housing 100', wherein the inner wall of the tip housing 100' defines a lumen for the tip bores to pass through to retain the marker band 120' within the tip housing 100'. As can be appreciated, the tip bore further increases the processing difficulty and cost. Therefore, how to reduce the processing difficulty and cost of an active cardiac electrical lead becomes a focus of research in this art.

The information included in this Background section of the specification, including any references cited herein and any description or discussion thereof, is included for technical reference purposes only and is not to be regarded subject matter by which the scope of the invention as defined in the claims is to be bound.

SUMMARY OF THE INVENTION

The objective of some embodiments of the present invention is to provide an active cardiac electrical lead to overcome the high processing difficulty, low yield and high cost problems with the conventional active cardiac electrical lead.

To solve these problems, an active cardiac electrical lead provided in some embodiments includes a tip housing having a lumen, a soft tip plug and a marker band. The tip housing includes a body and an extension extending from a distal end of the body, and the body has an outer diameter greater than an outer diameter of the extension. The soft tip plug fits over the extension and engages the extension. The marker band is attached to an outer surface of the body or to an inner surface of the lumen.

In some embodiments, in the active cardiac electrical lead, the marker band is located at a middle of the body, or at the distal end of the body, or at a location of the body spaced apart from the distal end thereof by a distance that is one-eighth to one-sixth of a length of the body. Alternatively, the marker band may be located at a middle of the lumen, or at the distal end of the lumen, or at a location of the lumen spaced apart from the distal end thereof by a distance that is one-eighth to one-sixth of a length of the lumen.

In some embodiments, in the active cardiac electrical lead, the marker band is attached to the outer surface of the body or the inner surface of the lumen by chemical bonding and/or mechanical connection.

In some embodiments, in the active cardiac electrical lead, a groove is defined in the outer surface of the body or in the inner surface of the lumen, the marker band is disposed in the groove.

In some embodiments, in the active cardiac electrical lead, an outer diameter of the marker band is congruent with a diameter of the outer surface of the body or with a diameter of the inner surface of the lumen.

In some embodiments, in the active cardiac electrical lead, an outer diameter of the soft tip plug is congruent with the outer diameter of the body.

In some embodiments, in the active cardiac electrical lead, the distal end of the body abuts against a proximal end of the soft tip plug.

In some embodiments, in the active cardiac electrical lead, the soft tip plug includes a sleeve bore, the sleeve bore has an inner surface with a diameter congruent with a diameter of an outer surface of the extension and an axial length congruent with an axial length of the outer surface of the extension.

In some embodiments, in the active cardiac electrical lead, the soft tip plug is engaged with the extension by means of a cross-linking agent.

In some embodiments, in the active cardiac electrical lead, the soft tip plug is mechanically fixed to the extension.

In some embodiments, in the active cardiac electrical lead, the soft tip plug is fixed to the extension by snapping.

In some embodiments, in the active cardiac electrical lead, the extension defines projection(s) at a distal end thereof, the projection(s) is disposed in a radial groove defined in the soft tip plug.

In some embodiments, in the active cardiac electrical lead, the number of the projection(s) is one and the projection is an annulus radially projecting from the extension.

In some embodiments, in the active cardiac electrical lead, the number of the projection(s) is at least two and the projections are equidistantly/symmetrically distributed circumferentially along the extension at the distal end thereof.

In some embodiments, in the active cardiac electrical lead, each of the projection(s) has a chamfered distal edge and a proximal face tapered with respect to the axial direction of the tip housing.

In some embodiments, in the active cardiac electrical lead, the soft tip plug further includes an edge portion at a proximal end thereof, the edge portion extends inward into an annular groove defined in the extension.

In some embodiments, in the active cardiac electrical lead, the radial groove includes an inner cylindrical surface, a proximal face in contact with the projection(s) and a shoulder abutting against a distal end of the projection(s), the inner cylindrical surface having a diameter greater than or equal to an outer diameter of the projection(s).

In some embodiments, in the active cardiac electrical lead, the edge portion includes an inner cylindrical surface, a proximal face in contact with the body of the tip housing and a distal face in contact with the projection(s), the inner cylindrical surface having a diameter that is greater than or equal to an outer diameter of the annular groove and is smaller than the outer diameter of the projection(s).

In some embodiments, in the active cardiac electrical lead, the lumen of the tip housing includes a sleeve bore at a proximal end thereof and a middle bore at a distal end thereof, the middle bore has a diameter smaller than a diameter of the sleeve bore, and wherein the marker band is attached to an inner surface of the middle bore.

In some embodiments, in the active cardiac electrical lead, the tip housing further includes an anchor guide extending radially inward from an inner surface of a middle bore.

The active cardiac electrical lead provided in some embodiments of the present invention includes a tip housing having a lumen, a soft tip plug and a marker band, the tip housing including a body and an extension extending from a distal end of the body, the body of greater outer diameter than the extension, the soft tip plug fitting over the extension and engaging the extension, the marker band is attached to an outer surface of the body or to an inner surface of the lumen. Such structural designs of the tip housing, soft tip plug and marker band enable sufficient adhesion between those components, while reducing process difficulty for the tip housing and the soft tip plug, increasing processing accuracy and yield for the soft tip plug and hence lowering the processing difficulty and cost for the active electrical lead.

BRIEF DESCRIPTION OF DRAWINGS

One or more embodiments are illustrated by way of example and not limitation in the figures of the accompanying drawings, in which like reference numerals indicate similar elements. The figures of the accompanying drawings do not constitute any limitation on scale, unless otherwise noted specifically.

In these figures,

10—lead; 12—proximal end; 14—distal end; 16—active tip portion; 100, 100'—tip housings; 101—body; 102—extension; 103—projection; 103'—projections; 104—annular groove; 105—lumen; 106—sleeve bore; 107—middle bore; 108—sleeve shoulder; 109—anchor guide; 110, 110'—soft tip plugs; 111—tip bore; 112—sleeve bore; 113—radially inward extending edge portion; 114—radial groove; 115—shoulder; 120, 120'—marker bands; 130—distal seal; 131—spacer/stopper; 140, 140'—helical anchor electrodes; 150—tip electrode pin; 151—proximal annular flange; 152—medial annular flange; 153—distal annular flange; 160—intermediate connection mount; 161—proximal fitting; 162—cylindrical flange; 163—distal fitting; 170—inner coil; 171—conductive connector pin; 172—connector insulator; 173—proximal seal; 180—outer coil; 181—ring connector; 182—insulator tubing; 183—boot seal; 190—ring electrode; and 200—outer sheath.

DETAILED DESCRIPTION OF EXEMPLARY EMBODIMENTS

An active cardiac electrical lead proposed in some embodiments of the present invention will be described below in greater detail with reference to the accompanying drawings and particular embodiments. Features and advantages of some embodiments of the invention will be more apparent from the following detailed description, and from the appended claims. It is noted that the figures are provided in a very simplified form not necessarily presented to scale, with the only intention to facilitate convenience and clarity in explaining some embodiments of the present invention.

Figure 1:
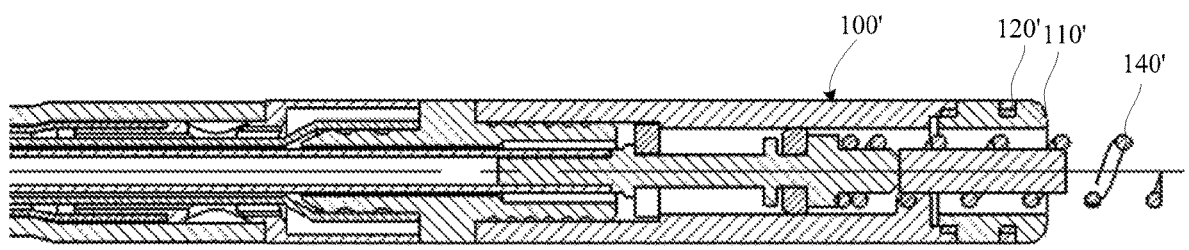
FIG. 1 is a cross-sectional view of a conventional active cardiac electrical lead with a helical electrode having extended out of a tip housing.
Figure 2:
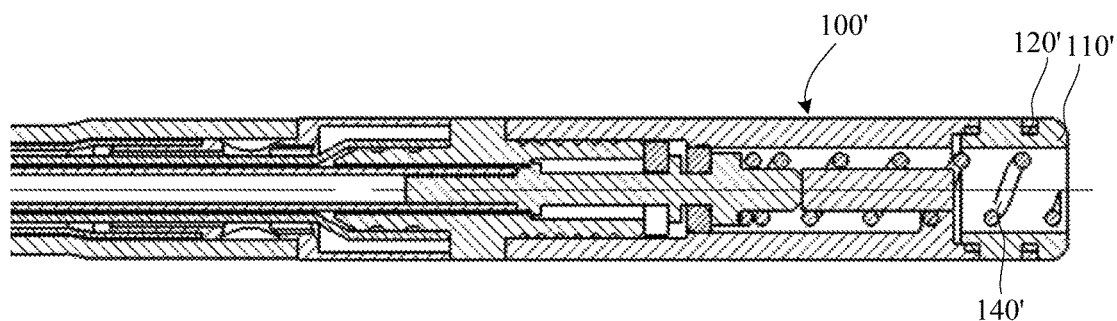
FIG. 2 is another cross-sectional view of the conventional active cardiac electrical lead, with the helical electrode retracted into the tip housing.
Figure 3:
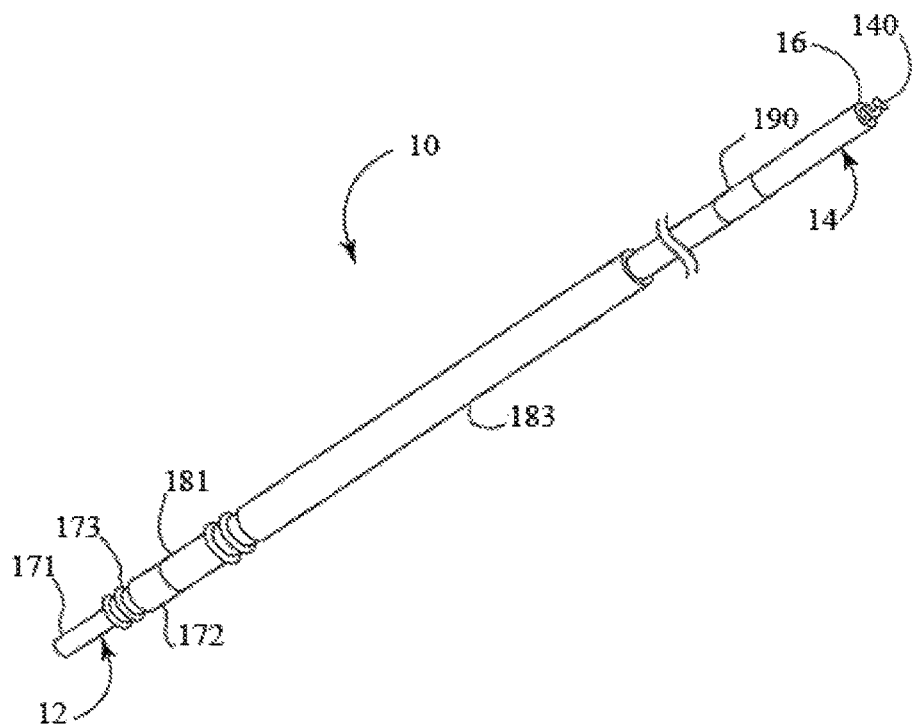
FIG. 3 is an isometric view of an exemplary embodiment of an implantable medical electrode lead with an active electrode.

FIG. 3 is an isometric view of one embodiment of an implantable medical electrode lead 10. The lead 10 has a proximal end 12 and a distal end 14. As shown in FIG. 3, an active tip portion 16 may be disposed at the distal end 14 of the lead 10, and may include a helical anchor electrode 140. The helical anchor electrode 140 may be designed to axially extend out of the active tip portion 16 to engage a treatment site of a patient such as the endocardium of a heart, for example. The helical anchor electrode 140 may be retractably extended distally out of the active tip portion 16. In operation, a conductive connector pin at the proximal end 12 of the lead 10 may be rotated to drive a mechanism in the active tip portion 16, thereby extending the helical anchor electrode 140 out of the tip portion 110. The rotating extension of the helical anchor electrode 140 from the active tip portion 16 may engage (i.e., screw into) a treatment site of a patient.

The proximal end 12 of the lead 10 includes a system of parts or pieces. The system of parts or pieces may be divided into three categories including inner parts relating to an inner conductor, outer parts relating to an outer conductor, and insulating parts for electrically separating the inner parts from the outer parts. The inner parts may include a conductive connector pin 171 and an inner coil 170. A distal end of the conductive connector pin 171 is mechanically and electrically connected to the inner coil 170 and is electrically connected to the helical anchor electrode 140 at the distal end 14 of the lead 10 via the inner coil 170. A proximal end of the conductive connector pin 171 may be configured for electrical engagement with a defibrillator, pacemaker or other electrical stimulation device and for communicating electrical impulses to the inner conductor or the inner coil 170. The outer parts may include a ring connector 181 and an outer coil 180. The ring connector 181 is mechanically and electrically connected to the outer coil 180 and is electrically connected to a ring electrode 190 at the distal end of the lead via the outer coil 180. The inner and outer parts may be substantially separated by the insulating parts including a connector insulator 172 and an insulator tubing 182. A proximal seal 173 and a boot seal 183 may also be provided.

The active electrode tip 16 at the distal end 14 of the lead 10 will be described in detail with reference to FIG. 4. The active electrode tip 16 may be considered to be composed of several primary components: a ring electrode 190, a tip electrode pin 150, a helical anchor electrode 140, an intermediate connection mount 160, a tip housing 100, a marker band 120 and a soft tip plug 110. Additional components may include a spacer/stopper 131 and a distal seal 130. A proximal end of the ring electrode 190 is electrically and mechanically connected to a distal end of the outer coil 180. A proximal end of the tip electrode pin 150 is electrically and mechanically connected to a distal end of the inner coil 170. A distal end of the tip electrode pin 150 is connected to a proximal end of the helical anchor electrode 140. The intermediate connection mount 160 connects the ring electrode 190 to the tip housing 100 to form an outer surface of the active electrode tip 16. A proximal portion of the tip electrode pin 150 and the helical anchor electrode 140 are substantially encased within the tip housing 100 when the helical anchor electrode 140 is in a retracted state. When the helical anchor electrode 140 is advanced, a distal tip of the helical anchor electrode 140 protrudes beyond the soft tip plug 110 in a distal end of the tip housing 100. Wherein the tip housing 100 includes a body 101 and an extension 102 at a distal end of the body 101 and the marker band 120 is disposed on the body 101, with the soft tip plug 110 fitting over the extension 102 so as to secure to and seal the extension 102.

Figure 5:
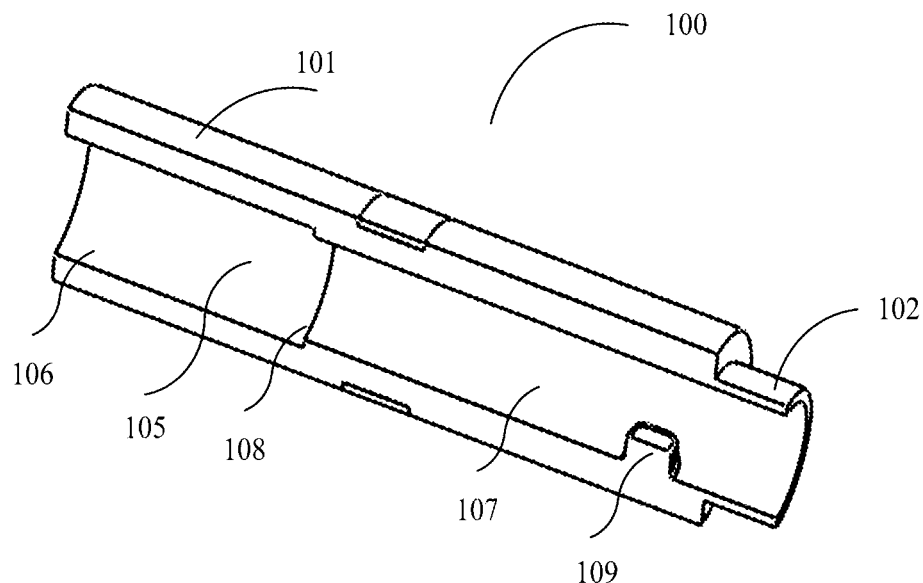
FIG. 5 is a front view of a tip housing according to some embodiments of the present invention.
Figure 5A:
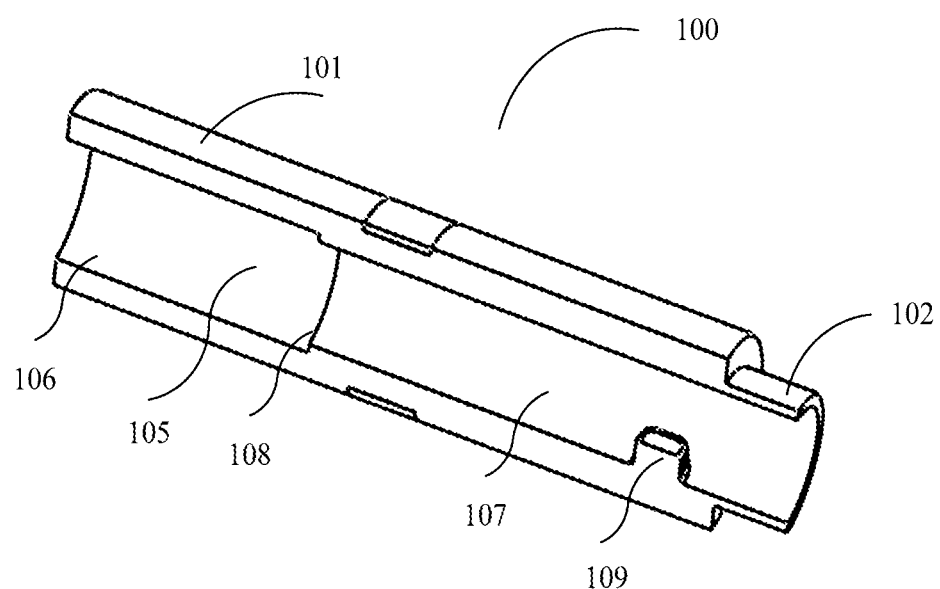
FIG. 5a is a cross-sectional view of FIG. 5.

Referring to FIGS. 5 and 5a, the tip housing 100 may include body 101 and an extension 102 at a distal end of the body 101. The body 102 of the tip housing 100 has an outer surface that may generally be either cylindrical or frustum-shaped. The tip housing 100 may be formed of a resilient biocompatible material (e.g., polyether ether ketone (PEEK) or polysulfone) in order to be fitted over the intermediate connection mount 160 and retained thereon.

The marker band 120 is secured on the outer surface of the body 101, and the securing may be accomplished by means of chemical adhesion and/or a mechanical mechanism such as, for example, an interference fit, insert molding, spot-welding together of the two ends of a C-shaped marker band, or an adhesive. In this embodiment, the marker band 120 is disposed at the middle of the body 101 and fits over the outer surface of the body 101 of the tip housing 100. Preferably, a groove is defined in the outer wall of the body 101 for accommodating the marker band 120. Preferably, the marker band 120 is of the same outer diameter as the body 101 at part thereof around the groove. The marker band 120 may be formed of a radiopaque material, e.g., a Pt/Ir alloy or a thermoplastic compound suitable for injection-molding and having an opacity to X-rays more than sufficient to guarantee shielding comparable to that of a metal. The marker band 120 provides a mark for a physician to identify under fluoroscopy the location of the distal end of the active electrode tip 16 allows the physician to determine whether the helical anchor electrode 140 is at retracted position or extension position or in between by comparing the position of the helical anchor electrode 140 to the marker band 120.

The extension 102 of the tip housing 100 has an outer surface that may generally be either cylindrical or frustum-shaped. A diameter of the extension 102 of the tip housing 100 is smaller than an outer diameter of the body 101 of the tip housing 100 at its distal end.

The active cardiac electrical lead 10 may further include a helical anchor electrode 140, a tip electrode pin 150, an intermediate connection mount 160 and a ring electrode 190. The tip housing 100 has a lumen 105 extending axially therethrough. The lumen 105 may define a sleeve bore 106 having a diameter greater than the diameter of the rest of the lumen (middle bore 107). The sleeve bore 106 may be sized in both diameter and length to sleeve over a distal fitting 163 of the intermediate connection mount 160 so as to accommodate the distal fitting 163 of the intermediate connection mount 160. The lumen 105 transitions at a sleeve shoulder 108 to a relatively long middle bore 107 of a narrower inner diameter. The middle bore 107 may receive the tip electrode pin 150 and the helical anchor electrode 140 and facilitate the extension and retraction of the tip electrode pin 150 and the helical anchor electrode 140. The middle bore 107 also acts as a sealing section to form a fluid tight seal with the distal seal 130 as further described below. An anchor guide 109 protrudes from a wall of the middle bore 107 at the distal end thereof and extends radially inward. The anchor guide 109 may be sized to fit between adjacent windings of the helical anchor electrode 140 and extend a distance slightly greater than a diameter (thickness) of the windings of the helical anchor electrode 140. As shown in the exemplary embodiment, the anchor guide 109 may be located at any position about the circumference of the middle bore 107. FIG. 4 also depicts an embodiment of the intermediate connection mount 160. The intermediate connection mount 160 has three primary sections: a proximal fitting 161, a cylindrical flange 162 and a distal fitting 163, wherein the cylindrical flange 162 is located between the proximal and distal fittings 161, 163. The intermediate connection mount 109 defines an axial lumen. The axial lumen passes through the intermediate connection mount 109 from the proximal end to the distal end. The proximal fitting 161 is received within a lumen of the ring electrode 190 to form a fixed connection. A proximal face of the cylindrical flange 162 abuts against a distal face of the ring electrode 190. The distal fitting 163 is received within the sleeve bore 106 of the tip housing 100 to form a fixed connection. A distal face of the cylindrical flange 162 abuts against a proximal face of the body 101 of the tip housing 100. Preferably, outer diameters of each of the cylindrical flange of the intermediate connection mount, an exposed section of the ring electrode and the tip housing are congruent. The lumen within the intermediate connection mount 109 may be formed in two parts, a proximal lumen and a distal lumen. The proximal lumen has an inner diameter that may be, for example, smaller than an inner diameter of the distal lumen but greater than a diameter of the inner coil 170.

It will be appreciated by those skilled in the art that the marker band 120 may be alternatively fixed to an inner surface of the lumen 105 of the tip housing 100. In this case, the marker band may be locate at the middle of the lumen, or at the distal end thereof, or at a position spaced from the distal end of the lumen by a distance that equals one-eighth (⅛) to one-sixth (⅙) of the lumen length. For example, the marker band may be fixed to the inner surface of the middle bore 107 by means of chemical adhesion and/or mechanically. For example, the inner surface of the middle bore 107 may define a groove in which the marker band 120 is received. The marker band 120 may be, for example, of the same inner diameter as the middle bore 107 at part thereof around the groove.

Figure 4:
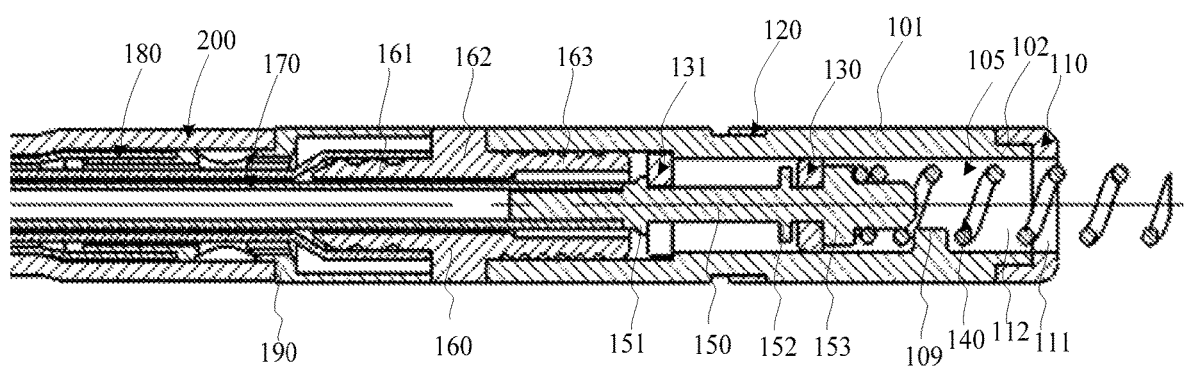
FIG. 4 is a cross-sectional view of a distal end of the lead of FIG. 3 with an active electrode tip.

FIG. 4 also depicts an embodiment of the tip electrode pin 150. The tip electrode pin 150 may be formed of a solid conducting material. The tip electrode pin 150 may be made, for example, of stainless steel (e.g., 316L), a precious metal (e.g., platinum or iridium), or a metal alloy (e.g., Pt/Ir or MP35N), or another electrically conductive, biocompatible material. The tip electrode pin 150 is generally cylindrical in shape with a number of shaft sections separated by a number of annular flanges. For example, the tip electrode pin 150 may be divided by a proximal annular flange 151 and a distal annular flange 153 into a proximal shaft section, a medial shaft section and a distal shaft section. The proximal shaft section is the section of the tip electrode pin 150 that engages the inner coil 170 and resides within the lumen of the intermediate connection mount 160. When the inner coil 170 is sleeved over the proximal shaft section, a diameter of the proximal shaft section is configured to allow the tip electrode pin 150 and attached inner coil 170 to freely rotate within the lumen of the intermediate connection mount 160. The distal shaft section of the tip electrode pin 150 is the section that connects with the proximal end of the helical anchor 140. The distal shaft section of the tip electrode pin 150 may be received in the middle bore 107 of the tip housing 100 and is freely rotatable therein. The proximal annular flange 151 may be received and freely rotate within the distal lumen of the intermediate connection mount 109. In one example, the proximal annular flange 151 may be of greater diameter than the medial shaft section. The distal annular flange 153 may be received and freely rotate within the middle bore 107 of the tip housing 100 and the distal annular flange 153 may have a diameter greater than that of the distal shaft section. The proximal end of the helical anchor 140 may abut against a distal face of the distal annular flange 153. In one example, the distal annular flange 153 may be of greater diameter than the medial shaft section.

In some embodiments, the active cardiac electrical lead may further include a spacer/stopper 131. The spacer/stopper 131 may be formed as a C shape with a gap in the ring allowing the ring to be installed about the medial shaft section of the tip electrode pin 150 from a side rather than axially. The spacer/stopper 131 defines a central aperture which, along with the gap, is sized in congruence with the medial shaft section of the tip electrode pin 150. The spacer/stopper 131 may be made of an electrically insulating material to reduce potential electrode electrical "chatter" that is known to occur in prior art designs with metallic components used in the control of advancement and retraction. For example, the spacer/stopper 113 may be made of polyethylene, polyether ether ketone (PEEK), or polysulfone, and may have a hardness of Shore 80 in order to provide appropriate flexibility to fit around the tip electrode pin 150 and appropriate resiliency to be retained thereon. The diameter of the spacer/stopper 113 is slightly smaller than the diameter of the sleeve bore 106 of the tip housing 100. The spacer/stopper 131 is ultimately housed in the tip housing 100. Specifically, the spacer/stopper 131 is confined within a space defined by the distal fitting 163 of the intermediate connection mount 160 and the sleeve bore 106 of the tip housing 100. In this manner, as the helical anchor electrode 140 is advanced out of and retracted into the tip housing 100, the spacer/stopper 113 can slide within the space defined by the distal fitting 163 of the intermediate connection mount 160 and the sleeve bore 106 of the tip housing 100 while helping maintain axial alignment of the helical anchor electrode 140 within the tip housing 100.

The spacer/stopper 131 is able to limit axially travel of the helical anchor electrode 140. When the spacer/stopper 131 is brought by the tip electrode pin 150 into contact with the distal fitting 163 of the intermediate connection mount 160, the helical anchor electrode 140 is blocked from further moving proximally. When the spacer/stopper 131 is brought by the tip electrode pin 150 (specifically, the proximal annular flange 151) into contact with a sleeve shoulder 108 of the tip housing 100, the helical anchor electrode 140 is blocked from further travelling distally.

In some embodiments, the active cardiac electrical lead may further include a distal seal 130. The distal seal 130 is substantially annular in shape. A medial annular flange 152 may be additionally arranged between the proximal and distal annular flanges 151, 153 of the tip electrode pin 150, and between the medial and distal annular flanges 152, 153 may be formed a seal shaft section. The distal seal 130 fits over the seal shaft section. The distal seal 130 may define a lumen that is sized in congruence with the seal shaft section. The distal seal 130 has an outer diameter that is slightly greater than the diameter of the middle bore 107 of the tip housing 100 so as to allow the establishment of a fluid-tight seal with the middle bore 107. The distal seal 130 may be made of an elastomeric material that is flexible and resilient enough to fit over the tip electrode pin 150 while achieving a good seal. In this case, the helical anchor electrode 140 may be driven to move proximally by the medial annular flange 152 instead of the distal annular flange 153.

A further description of the soft tip plug 110 will be set forth below with reference to FIG. 4. The soft tip plug 110 may be formed of a molded, biocompatible, elastomeric material designed to minimize trauma to vasculature and tissue, including lead perforation, as the lead 10 is positioned for implantation. In some embodiments, the soft tip plug 110 may be coated with a steroid (e.g., dexamethasone) for relieving inflammation at the implant location or with other medicinal agents. The soft tip plug 110 may have a substantially cylindrical or frustum-shaped outer surface. Preferably, a proximal end of the soft tip plug 110 is of the same outer diameter as the distal end of the body 101 of the tip housing 100. The soft tip plug 110 may be provided with a lumen penetrating therethrough. At least part of the helical anchor electrode 140 may be received in the lumen of the soft tip plug 110 when the helical anchor electrode 140 extends out. The lumen of the soft tip plug 110 may be composed of a proximal sleeve bore 112 and a distal tip bore 111. The lumen of the soft tip plug 110 may transition from the sleeve bore 112 to the tip bore 111 at a shoulder 115. An inner diameter of the sleeve bore 112 may be congruent with the outer diameter of the extension 102 of the tip housing 100. The inner surface of the tip bore 111 may be of substantially the same diameter as that of the inner surface of the middle bore 107. In order to ensure a good seal between the soft tip plug 110 and the tip housing 100, the sleeve bore 112 may have an axial length that is congruent with an axial length of the extension 102 in the tip housing 100. The lumen wall of the soft tip plug 110 may come into contact and be fixedly glued to the extension 102 of the tip housing 100 using a cross-linking agent. The present invention is not limited to any particular cross-linking agent, as long as it is harmless to the human body. The tip housing 100 shown in FIGS. 6, 8, 9 and 11 is similar to that of FIG. 5, except that in addition to the cross-linking agent, the fixation between the soft tip plug 110 and the extension 102 of the tip housing 100 is further intensified by means of respective different mechanical actions.

Figure 6:
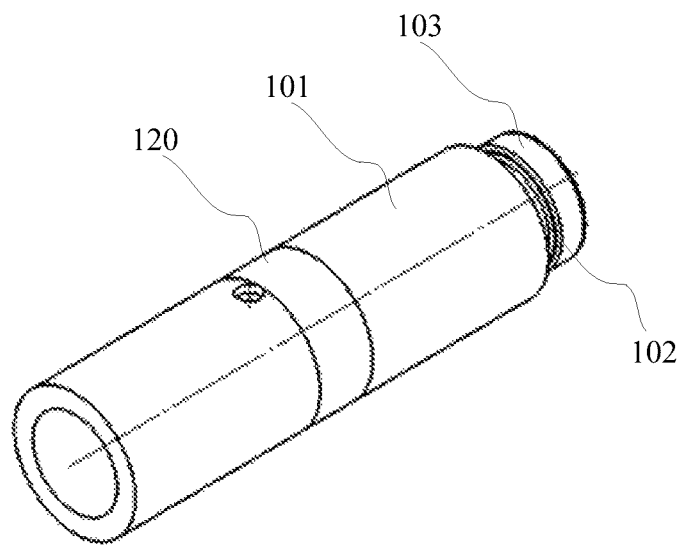
FIG. 6 is a front view of a tip housing with a marker band disposed at the middle thereof according to a first embodiment of the present invention.
Figure 6A:
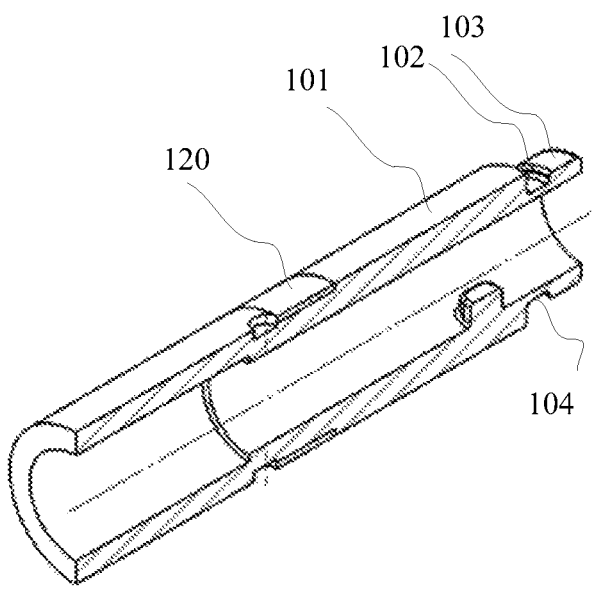
FIG. 6a is a cross-sectional view of FIG. 6.

As shown in FIGS. 6 and 6a, the tip housing 100 may has an annular radially-extending projection 103 at the distal end of the extension 102 and an annular groove 104 defined at the proximal end of the extension 102. For ease of fitting and engagement, the projection 103 may have a chamfered distal edge. The projection 103 may also have a proximal edge that is tapered with respect to the axis of the tip housing 100 in order for a larger contact area with the soft tip plug 110 to be obtained.

Figure 7:
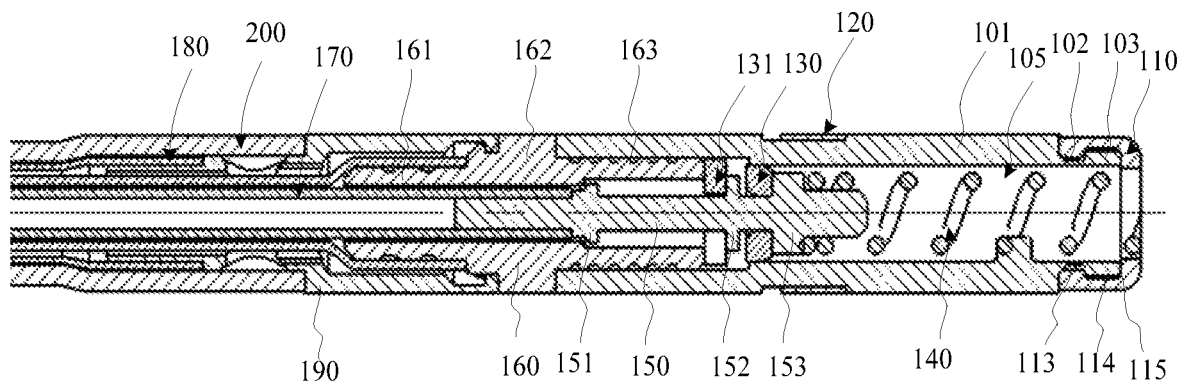
FIG. 7 is a cross-sectional view of an active cardiac electrical lead with the tip housing of FIG. 6.

As shown in FIG. 7, the soft tip plug 110 may have an edge portion 113 at its proximal end, which extends radially inward into the annular groove 104 of the extension 102. The edge portion 113 may include an inner cylindrical surface, a proximal face and a distal face in contact with the projection 103 of the extension 102. In order to achieve a large contact area with the projection, the distal face may be tapered. The inner cylindrical surface may have a diameter that is greater than or equal to an outer diameter of the annular groove 104 in the extension 102 but smaller than an outer diameter of the projection 203. The proximal face of the edge portion 113 may abut against the distal face of the body 101 of the tip housing 100 in order to attain a good seal between the soft tip plug 110 and the tip housing 100. With the edge portion 113, the rest of the sleeve bore 112 of the soft tip plug 110 defines a radial groove 114, wherein the radial groove 114 includes an inner cylindrical surface, a proximal face in contact with the projection 103, and a shoulder 115. The projection 103 is received in the radial groove 114. The inner cylindrical surface of the radial groove 114 may have a diameter that is greater than or equal to an outer diameter of the projection 103. For example, the distal face of the projection 103 may abut against the shoulder 115.

Figure 8:
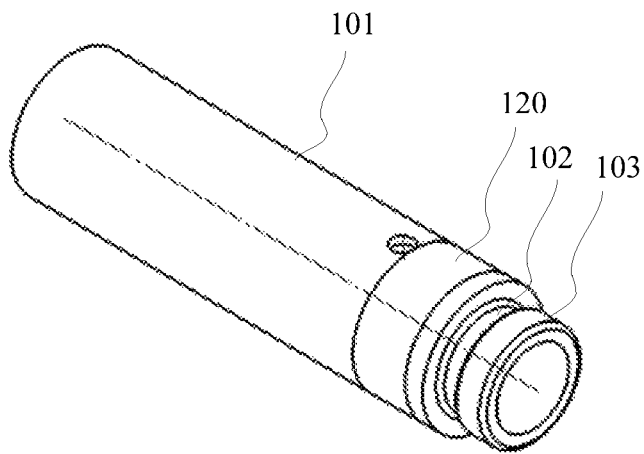
FIG. 8 is a front view of the tip housing with the marker band disposed close to its distal end in the first embodiment of the present invention.
Figure 8A:
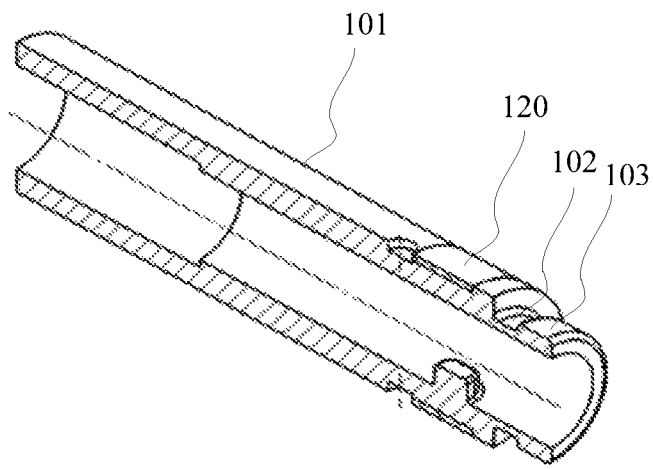
FIG. 8a is a cross-sectional view of FIG. 8.
Figure 9:
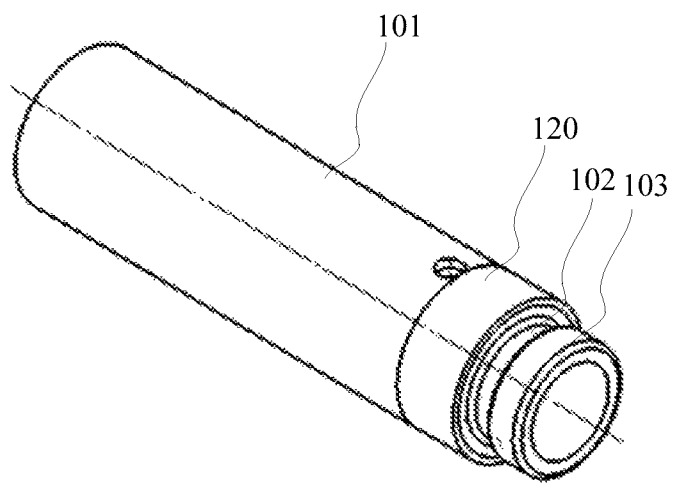
FIG. 9 is a front view of the tip housing with the marker band disposed at its distal end in the first embodiment of the present invention.
Figure 9A:
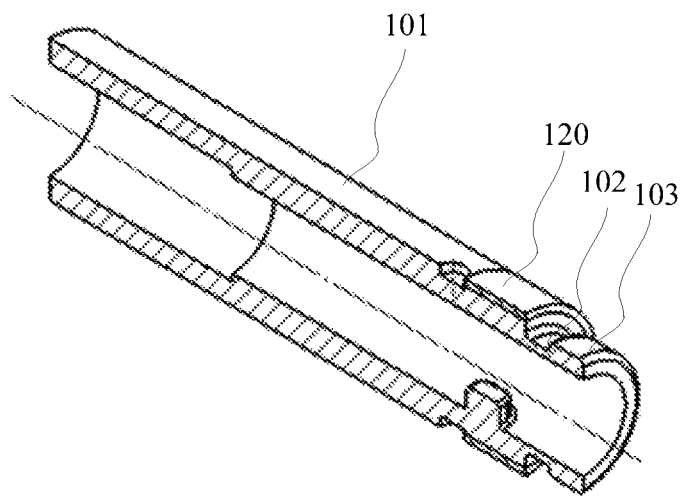
FIG. 9a is a cross-sectional view of FIG. 9.
Figure 10:
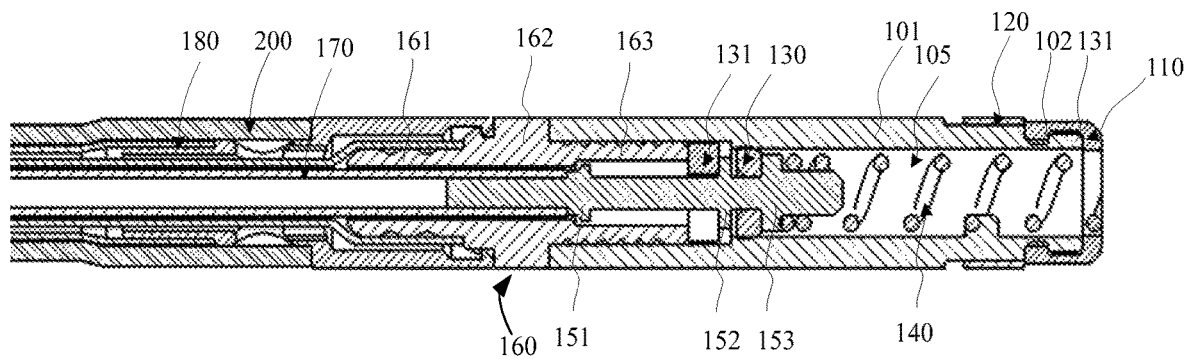
FIG. 10 is a cross-sectional view of the active cardiac electrical lead with the tip housing of FIG. 9.

The tip housing 100 shown in FIGS. 8 and 9 is similar to that of FIG. 6, except that the marker band 120 is disposed at respective different positions of the tip housing 100. As shown in FIGS. 8 and 8a, the marker band 120 may be disposed at a position close to the distal end of the body 101 of the tip housing 100, for example, one-eighth to one-sixth of a length of the body 101 away from the distal end thereof. As shown in FIGS. 9 and 9a, the marker band 120 may be alternatively disposed at the distal end of the body 101 of the tip housing 100. It will be appreciated by those skilled in the art that no matter where the marker band 120 is disposed on the tip housing 100, the performance of the active cardiac electrical lead will not be affected and the variations in the position of the marker band only shift the reference point against which the distance the helical anchor electrode 140 is extended or retracted is measured.

Figure 11:
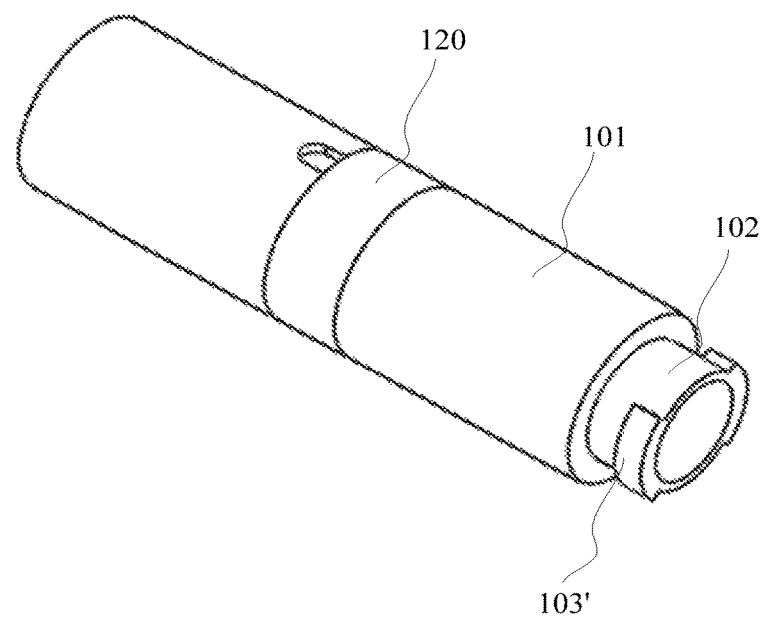
FIG. 11 is a front view of a tip housing with a marker band disposed at the middle thereof according to a second embodiment of the present invention.
Figure 12:
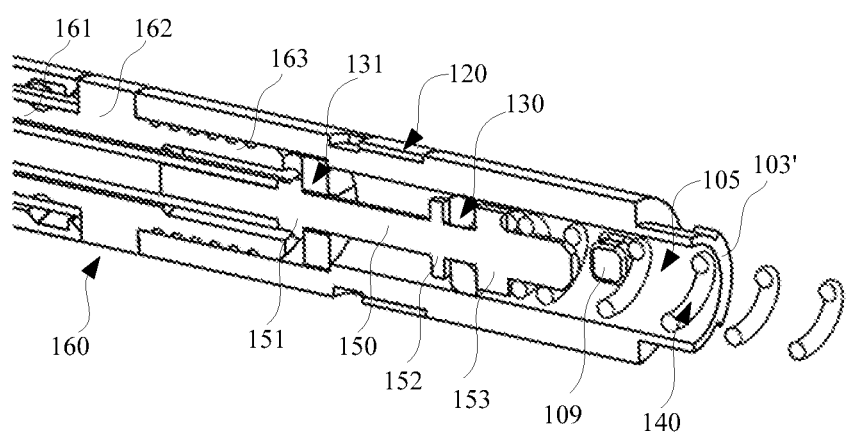
FIG. 12 is a cross-sectional view of the active cardiac electrical lead with the tip housing of FIG. 11.

FIG. 11 shows another embodiment of the tip housing 100, which is similar to that of FIG. 6, except that the extension 102 of the tip housing 100 is modified to reduce the interlocking strength of the snap-on coupling mechanism. Differing from the single annular projection 103 of FIG. 6, a plurality of projections 103' are defined at the distal end of the extension in the embodiment of FIG. 11. The number of the projections 103' may be at least two, at least three, at least four or at least five. The projections may be equidistantly/symmetrically distributed circumferentially at the distal end of the extension 102. Specifically, in the embodiment shown in FIG. 11, the marker band 120 is disposed around the middle of the body 101, and two projections 103' are defined at the distal end of the extension 102 and received in the radial groove 114 of the soft tip plug 110. The two projections 103' each extend along part of the circumference of the extension 102 at the distal end and are distributed symmetrically. Reference can be made further to FIG. 12 for a better understanding of the tip housing 100 in the active cardiac electrical lead. It can be seen from a comparison of FIGS. 12 and 7 that except for the projections of the extension 102, the rest of the active cardiac electrical lead remains the same in term of position and structure as that of FIG. 7, and a further description is therefore deemed unnecessary.

The embodiments disclosed herein are described in a progressive manner, with the emphasis on explaining each of them focusing on its differences from the others. Reference can be made between the embodiments for their sameness and similarities.

In summary, the active cardiac electrical lead provided in some embodiments of the present invention includes a tip housing having a lumen, a soft tip plug and a marker band, the tip housing including a body and an extension extending from a distal end of the body, the body of greater outer diameter than the extension, the soft tip plug fitting over the extension so that it seals and is secured to the extension, the marker band fixed to an outer surface of the body or to an inner surface of the lumen. Such structural designs of the tip housing, soft tip plug and marker band enable sufficient adhesion between those components, while reducing process difficulty for the tip housing and the soft tip plug, increasing processing accuracy and yield for the soft tip plug and hence lowering the processing difficulty and cost for the active electrical lead.

The description presented above is merely that of a few embodiments of the present invention and will not limit the scope of the invention in any way. Any and all changes and modifications made by those of ordinary skill in the art based on the above teachings fall within the scope as defined in the appended claims.

What is claimed is:

1. An active cardiac electrical lead, comprising a tip housing having a lumen, a soft tip plug and a marker band, the tip housing comprising a body and an extension extending from a distal end of the body, the body having an outer diameter greater than an outer diameter of the extension, the soft tip plug fitting over the extension and engaging the extension by means of a cross-linking agent, the marker band attached to an outer surface of the body or to an inner surface of the lumen, wherein the marker band does not have any holes formed in a wall thereof,
   wherein the extension defines projection(s) at a distal end thereof and an annular groove at a proximal end thereof, wherein the soft tip plug defines a radial groove at a distal end thereof and an edge portion at a proximal end thereof, the projection(s) disposed in the radial groove defined in the soft tip plug, and the edge portion extending inward into the annular groove defined in the extension.

2. The active cardiac electrical lead according to claim 1, wherein the marker band is located at a middle of the body, or at the distal end of the body, or at a location of the body spaced apart from the distal end thereof by a distance of one-eighth to one-sixth of a length of the body; or
   the marker band is located at a middle of the lumen, or at a distal end of the lumen, or at a location of the lumen spaced apart from the distal end thereof by a distance of one-eighth to one-sixth of a length of the lumen.

3. The active cardiac electrical lead according to claim 1, wherein the marker band is attached to the outer surface of the body or the inner surface of the lumen by chemical bonding and/or mechanical connection.

4. The active cardiac electrical lead according to claim 1, wherein a groove is defined in the outer surface of the body or in the inner surface of the lumen, the marker band being disposed in the groove.

5. The active cardiac electrical lead according to claim 4, wherein an outer diameter of the marker band is congruent with a diameter of the outer surface of the body or with a diameter of the inner surface of the lumen.

6. The active cardiac electrical lead according to claim 1, wherein an outer diameter of the soft tip plug is congruent with the outer diameter of the body.

7. The active cardiac electrical lead according to claim 1, wherein the distal end of the body abuts against a proximal end of the soft tip plug.

8. The active cardiac electrical lead according to claim 1, wherein the soft tip plug comprises a sleeve bore, the sleeve bore having an inner surface with a diameter congruent with a diameter of an outer surface of the extension and an axial length congruent with an axial length of the outer surface of the extension.

9. The active cardiac electrical lead according to claim 1, wherein a number of the projection(s) is one and the projection is an annulus radially projecting from the extension.

10. The active cardiac electrical lead according to claim 9, wherein each of the projection(s) has a chamfer on a tip of the distal end thereof and a face of a proximal end thereof inclining to an axial direction of the tip housing.

11. The active cardiac electrical lead according to claim 1, wherein a number of the projection(s) is at least two and the projections are equidistantly/symmetrically distributed circumferentially along the extension at the distal end thereof.

12. The active cardiac electrical lead according to claim 1, wherein the radial groove comprises an inner cylindrical surface, a proximal face in contact with the projection(s) and a shoulder abutting against a distal end of the projection(s), the inner cylindrical surface having a diameter greater than or equal to an outer diameter of the projection(s).

13. The active cardiac electrical lead according to claim 1, wherein the edge portion comprises an inner cylindrical surface, a proximal face in contact with the body of the tip housing and a distal face in contact with the projection(s), the inner cylindrical surface having a diameter greater than or equal to an outer diameter of the annular groove and is smaller than the outer diameter of the projection(s).

14. The active cardiac electrical lead according to claim 1, wherein the lumen of the tip housing comprises a sleeve bore at a proximal end thereof and a middle bore at a distal end thereof, the middle bore having a diameter smaller than a diameter of the sleeve bore, and wherein the marker band is attached to an inner surface of the middle bore.

15. The active cardiac electrical lead according to claim 1, wherein the tip housing further comprises an anchor guide extending radially inward from an inner surface of a middle bore.

* * * * *